US006916463B2

(12) United States Patent
Lee et al.

(10) Patent No.: US 6,916,463 B2
(45) Date of Patent: Jul. 12, 2005

(54) ORAL PRODUCTS HAVING AN AESTHETIC LAYER

(75) Inventors: Kuo-Chung Mark Lee, Hamilton, OH (US); Gary Lyle Walden, West Chester, OH (US); Hooman Shahidi, Mason, OH (US); Christopher Robert Mayer, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/253,138

(22) Filed: Sep. 24, 2002

(65) Prior Publication Data

US 2004/0057910 A1 Mar. 25, 2004

(51) Int. Cl.[7] ............................. A61K 7/16; A61K 7/18; A61K 7/20
(52) U.S. Cl. .......................... 424/53; 424/49; 424/401; 424/443; 433/89; 433/136; 433/138; 433/215; 433/216; 433/217.1; 433/226; 433/227; 433/228.1
(58) Field of Search ........................ 433/89, 136, 138, 433/215, 216, 217.1, 226, 227, 228.1; 424/401, 443, 49–58

(56) References Cited

U.S. PATENT DOCUMENTS

| | | | |
|---|---|---|---|
| 2,835,628 A | | 5/1958 | Satfir |
| 4,517,173 A | | 5/1985 | Kizawa et al. |
| 4,590,075 A | | 5/1986 | Wei et al. |
| 4,623,394 A | | 11/1986 | Nakamura et al. |
| 4,713,243 A | | 12/1987 | Schiraldi et al. |
| 4,900,552 A | | 2/1990 | Sanvordeker et al. |
| 4,983,404 A | | 1/1991 | Raman et al. |
| 5,236,685 A | | 8/1993 | Fuchs et al. |
| 5,252,577 A | | 10/1993 | Breuer et al. |
| 5,266,335 A | | 11/1993 | Cherukuri et al. |
| 5,326,685 A | * | 7/1994 | Gaglio et al. ............... 433/215 |
| 5,411,945 A | | 5/1995 | Ozaki et al. |
| 5,425,953 A | | 6/1995 | Sintov et al. |
| 5,451,401 A | | 9/1995 | Zerby et al. |
| 5,458,879 A | | 10/1995 | Singh et al. |
| 5,498,439 A | | 3/1996 | Bonner |
| 5,571,782 A | | 11/1996 | Trinh et al. |
| 5,575,654 A | * | 11/1996 | Fontenot ..................... 433/215 |
| 5,607,708 A | | 3/1997 | Fraser et al. |
| 5,626,866 A | | 5/1997 | Ebert et al. |
| 5,628,986 A | * | 5/1997 | Sanker et al. ................. 424/49 |
| 5,629,003 A | | 5/1997 | Horstmann et al. |
| 5,679,389 A | | 10/1997 | Wong et al. |
| 5,700,478 A | | 12/1997 | Biegajski et al. |
| 5,759,599 A | | 6/1998 | Wampler et al. |
| 5,851,551 A | | 12/1998 | Tseng et al. |
| 5,863,202 A | | 1/1999 | Fontenot et al. |
| 5,879,691 A | | 3/1999 | Sagel et al. |
| 5,891,453 A | | 4/1999 | Sagel et al. |
| 5,894,017 A | | 4/1999 | Sagel et al. |
| 5,948,430 A | | 9/1999 | Zerbe et al. |
| 5,968,633 A | | 10/1999 | Hamilton et al. |
| 5,980,249 A | | 11/1999 | Fontenot |
| 5,989,569 A | | 11/1999 | Dirksing et al. |
| 6,026,829 A | * | 2/2000 | Mitha et al. ................. 132/321 |
| 6,045,811 A | | 4/2000 | Dirksing et al. |
| 6,096,328 A | * | 8/2000 | Sagel et al. ................... 424/53 |
| 6,099,940 A | | 8/2000 | Hamilton et al. |
| 6,121,315 A | | 9/2000 | Nair et al. |
| 6,136,297 A | | 10/2000 | Sagel et al. |
| 6,177,096 B1 | | 1/2001 | Zerbe et al. |
| 6,261,540 B1 | | 7/2001 | Nelson |
| 6,277,401 B1 | * | 8/2001 | Bello et al. .................. 424/449 |
| 6,277,458 B1 | | 8/2001 | Dirksing et al. |
| 6,284,264 B1 | | 9/2001 | Zerbe et al. |
| 6,287,603 B1 | | 9/2001 | Prasad et al. |
| 6,312,671 B1 | | 11/2001 | Jensen et al. |
| 6,322,774 B1 | | 11/2001 | Jensen et al. |
| 6,343,932 B1 | | 2/2002 | Wiesel |
| 6,419,906 B1 | * | 7/2002 | Xu et al. ....................... 424/53 |
| 6,461,158 B1 | | 10/2002 | Sagel et al. |
| 6,471,947 B2 | * | 10/2002 | Bhakoo et al. ................ 424/53 |
| 6,475,472 B2 | * | 11/2002 | Joiner et al. ................... 424/53 |
| 6,503,486 B2 | * | 1/2003 | Xu et al. ....................... 424/53 |
| 6,505,965 B1 | * | 1/2003 | McGovern ................... 378/169 |

(Continued)

FOREIGN PATENT DOCUMENTS

| | | |
|---|---|---|
| DE | 1104116 | 4/1961 |
| EP | 0 328 317 A1 | 8/1989 |
| EP | 1 008 343 A1 | 6/2000 |
| GB | 2 134 441 | 8/1984 |
| JP | 5-236885 | 9/1993 |
| WO | WO 95/07683 | 3/1995 |
| WO | WO 00/18365 | 4/2000 |
| WO | WO 01/07507 | 2/2001 |
| WO | WO 01/48024 | 7/2001 |
| WO | WO 01/70194 | 9/2001 |
| WO | WO 03/00 216 | 1/2003 |
| WO | WO 03/000216 A1 | 1/2003 |
| WO | WO 03/015656 A2 | 2/2003 |

OTHER PUBLICATIONS

U.S. Appl. No. 10/410,037, filed Apr. 9, 2003, Sagel et al.

U.S. Appl. No. 10/154,020, filed May 23, 2002, Sagel et al.

U.S. Appl. No. 10/659,100, filed Sep. 10, 2003, Sagel et al.

Primary Examiner—Frederick Krass
(74) Attorney, Agent, or Firm—James C. Vago; Karen F. Clark

(57) ABSTRACT

A packaged tooth whitening product is provided. The package includes a substrate having a first side and a second side, wherein the substrate is sized for use in a human user's oral cavity. A first composition including a tooth whitening agent is disposed adjacent the first side of the substrate. A second composition including an aesthetic agent disposed adjacent the second side of the substrate.

20 Claims, 6 Drawing Sheets

U.S. PATENT DOCUMENTS

| | | |
|---|---|---|
| 6,509,007 B2 * | 1/2003 | Rajaiah et al. ................. 424/53 |
| 6,514,483 B2 * | 2/2003 | Xu et al. ....................... 424/53 |
| 6,514,484 B2 * | 2/2003 | Rajaiah et al. ................. 424/53 |
| 6,551,579 B2 | 4/2003 | Sagel et al. |
| 6,582,708 B1 * | 6/2003 | Sagel et al. ................... 424/53 |
| 6,607,382 B1 * | 8/2003 | Kuo et al. ................. 433/216 |
| 6,612,429 B2 * | 9/2003 | Dennen ..................... 206/268 |
| 6,688,766 B2 * | 2/2004 | Gant et al. ................... 378/169 |
| 2001/0022964 A1 | 9/2001 | Leung et al. |
| 2001/0046511 A1 | 11/2001 | Zerbe et al. |
| 2002/0006388 A1 | 1/2002 | Sagel et al. |
| 2002/0146666 A1 | 10/2002 | Sagel et al. |
| 2003/0059381 A1 | 3/2003 | Goodhart et al. |
| 2003/0068284 A1 | 4/2003 | Sagel et al. |

* cited by examiner

ORAL PRODUCTS HAVING AN AESTHETIC LAYER

TECHNICAL FIELD OF THE INVENTION

The present invention relates to oral products having an aesthetic layer, and, more particularly, to tooth whitening products having an aesthetic layer.

BACKGROUND OF THE INVENTION

Tooth whitening has become very popular over the past few years. More and more consumers are choosing to whiten their teeth. Options for tooth whitening include toothpastes, mouth rinses, chewing gums, in-office bleaching, and most commonly tooth whitening solutions used with a tray obtained either over-the-counter or from a dentist. Tooth whitening products using a strip of material in combination with a chemical whitening agent are known in the art. For example, U.S. Pat. Nos. 5,891,453 and 5,879,691, the substances of which are incorporated herein by reference, describe a whitening product comprising a flexible strip of material and a tooth whitening composition with a peroxide agent and carboxypolymethylene gelling agent. While peroxide and carboxypolymethylene are common ingredients in tooth whitening applications, one or both can contribute to an undesirable taste sensation during use. As such, there is a desire for tooth whitening products having an aesthetic agent that improves the oral experience. However, the peroxide agent, along with other constituents of the tooth whitening product (e.g., water in the tooth whitening composition, materials in the package storing the strip of material), can be reactive with potential aesthetic agents, such as aromatic agents, sensate agents, and flavoring agents. Thus, there is also a desire for tooth whitening products having an aesthetic agent that improves the oral experience where the aesthetic agent is stable over an extended period of storage.

SUMMARY OF THE INVENTION

A packaged tooth whitening product is provided. The package includes a substrate having a first side and a second side, wherein the substrate is sized for use in a human user's oral cavity. A first composition including a tooth whitening agent is disposed adjacent the first side of the substrate. A second composition including an aesthetic agent disposed adjacent the second side of the substrate.

BRIEF DESCRIPTION OF THE DRAWINGS

While the specification concludes with claims particularly pointing out and distinctly claiming the invention, it is believed that the present invention will be better understood from the following description taken in conjunction with the accompanying drawings in which:

DETAILED DESCRIPTION OF THE PREFERRED EMBODIMENTS

Reference will now be made in detail to the present preferred embodiments of the invention, examples of which are illustrated in the accompanying drawings wherein like numerals indicate the same elements throughout the views and wherein elements having the same two last digits (e.g., 20 and 120) connote similar elements. While the present invention will be described herein with respect to a tooth whitening strip such as that described in U.S. Pat. Nos. 5,891,453 and 6,419,906, the substances of which are incorporated herein by reference, it is contemplated that the present invention can be used with other tooth whitening products as well as other oral products as described more fully hereafter.

Figure 1:
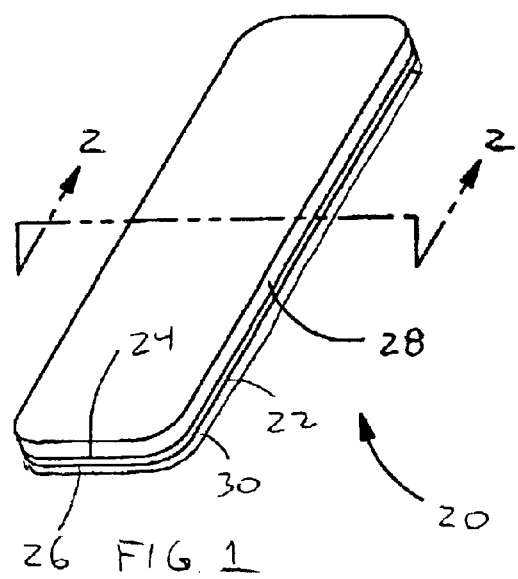
FIG. 1 is a perspective view of a tooth whitening product made in accordance with the present invention.
Figure 2:
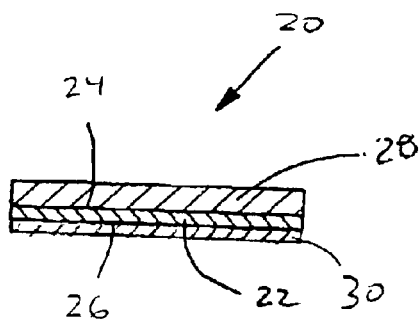
FIG. 2 is cross-sectional side view of the tooth whitening product of FIG. 1, taken along line 2—2 thereof.
Figure 3:
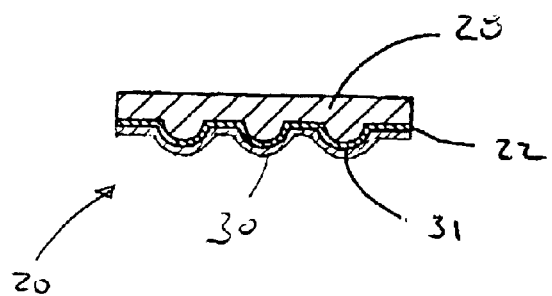
FIG. 3 is a cross-sectional side view of an alternate embodiment of the tooth whitening product of FIG. 1, wherein a plurality of pockets are shown.
Figure 4:
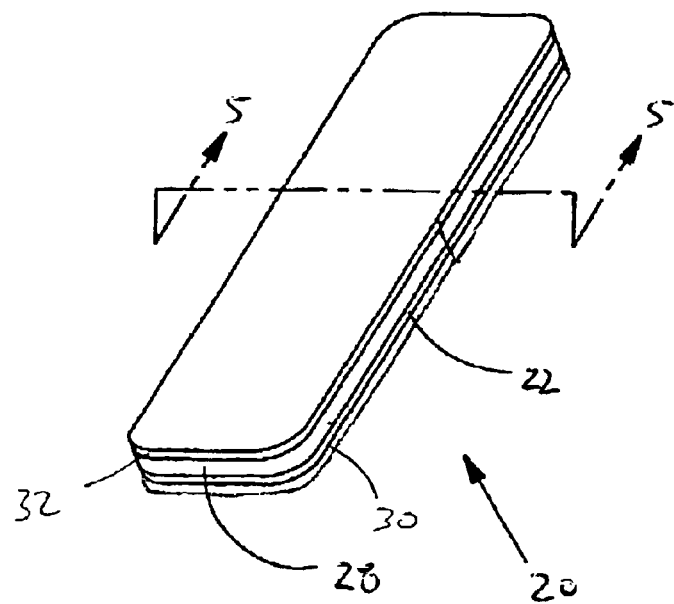
FIG. 4 is a perspective view of the tooth whitening product of FIG. 1 further including a release liner.
Figure 5:
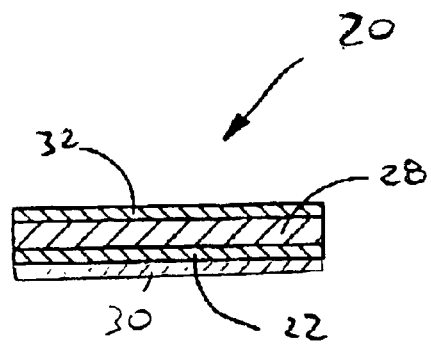
FIG. 5 is a cross-sectional side view of the tooth whitening product of FIG. 4, taken along line 5—5 thereof.
Figure 6:
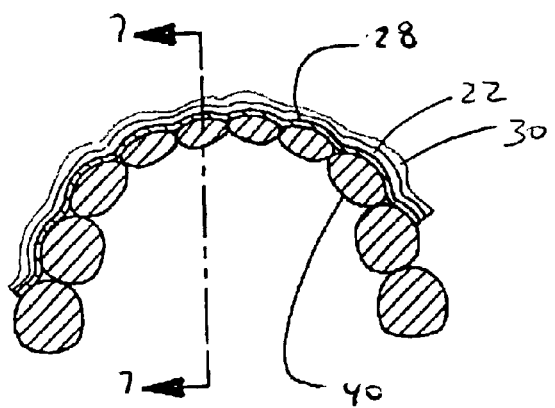
FIG. 6 is a cross-sectional plan view of a plurality of teeth having the tooth whitening product of FIG. 1 applied thereto, wherein the tooth whitening product is applied to the front or labial surface of the teeth.
Figure 7:
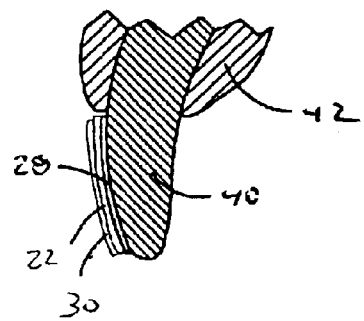
FIG. 7 is a cross-sectional side view of the teeth and tooth whitening product of FIG. 6, taken along line 7—7 thereof.
Figure 8:
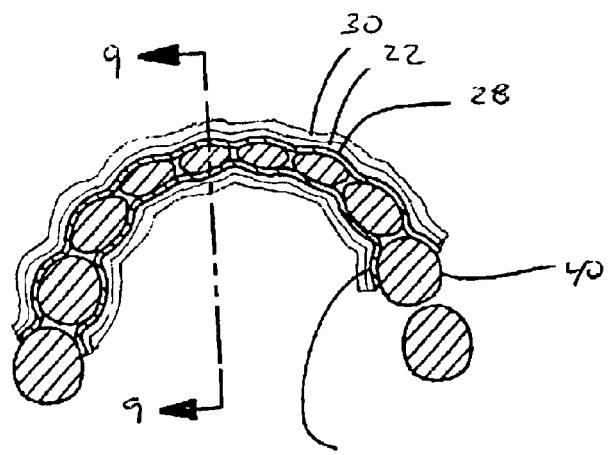
FIG. 8 is a is a cross-sectional plan view of a plurality of teeth having the tooth whitening product of FIG. 1 applied thereto, wherein the tooth whitening product is applied to the front or labial surfaces of the teeth and the rear or lingual surfaces of the teeth and soft tissue adjacent the labial surfaces of the teeth.
Figure 9:
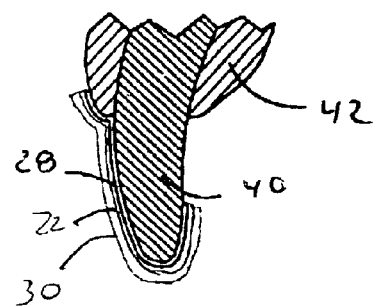
FIG. 9 is a cross-sectional side view of the teeth and tooth whitening product of FIG. 8, taken along line 9—9 thereof.

Referring to FIGS. 1, 2, and 3, an exemplary tooth whitening product 20 made in accordance with the present invention will now be described. The tooth whitening product 20 comprises a substrate 22 having a first side 24 and a second side 26, a first layer 28 formed from a first composition disposed adjacent the first side 24, and a second layer 30 formed from a second composition disposed adjacent the second side 26. Optionally, an array or plurality of substantially unshaped pockets 31 can be formed in the substrate 22. The pockets are filled with the first composition and provide a texture to the substrate. Since the pockets are formed in the substrate, the array of pockets is generally planar in nature. Also optionally, one or both sides of the first and second layers that are opposite the substrate 22 can be covered by a release liner 32, as shown by way of example in FIGS. 4 and 5, or one or both sides 31 of the first and second layers can be exposed. In one embodiment, the first composition is a tooth whitening composition, and the second composition includes an aesthetic agent. While the present invention will be described with respect to a tooth whitening composition, it will be appreciated that the first composition can be provided in other forms. For example, phosphates, flouride ion sources, anti-microbial agents, anti-inflammatory agents, nutrients, enzymes, anti-oxidants, H-2 antagonists, and so forth can be used in place of a tooth whitening agent. These and other oral care agents that are suitable for use with the present invention are described in U.S. Pat. No. 6,136,297, the substance of which is incorporated herein by reference.

The tooth whitening composition can be coated or spread on the substrate 22, and it forms a first layer 28 having a thickness at least about 0.01 mm, or at least about 0.02 mm, or at least about 0.05 mm, or at least about 0.07 mm and/or less than about 0.05 mm, or less than about 1 mm, or less than about 2 mm, or less than about 3 mm. These measurements are taken by measuring from the surface of the substrate 22 and up through the first layer 28. While it is desirable for the first layer 28 to be a homogeneous, uniform and continuous layer, the first layer 28 may also be non-uniform, non-continuous, and/or heterogeneous. For example, the first layer 28 can be a laminate or separated layers of components, an amorphous mixture of components, separate stripes or spots or other patterns of different components, or a combination of these structures. Further, the first layer can be formed as part of or intermixed with the substrate 22. Alternatively, the first composition can be substituted for the substrate 22, such as described by way of example in U.S. Pat. No. 6,419,906. For example, the first composition could be provided in the form of a film or strip comprising a water hydratable ethylene oxide polymer having a tooth whitening agent incorporated therein. The second layer 30 incorporating the aesthetic agent could then be formed as a film adjacent one side of the ethylene oxide polymer film. As used herein, the phrase "disposed adjacent" is intended to refer to placement directly on the subject surface or it can include placement near the subject surface such as where there is an intermediate additional coating. For example, there could be a coating material disposed between the second layer 30 incorporating the aesthetic agent and the ethylene oxide polymer film.

The tooth whitening composition that forms the first layer 28 can be provided in the form of a viscous liquid, paste, gel, solution, solid, or any other state or phase that can form a layer. In one embodiment, the tooth whitening composition is provided in the form of a gel and has a viscosity between about 200 and about 1,000,000 cps at low shear rates (approximately one seconds$^{-1}$), and in another embodiment the viscosity is between about 100,000 and about 800,000 cps. In other embodiments, the viscosity is between about 150,000 and about 700,000 cps or between about 300,000 and about 700,000 cps.

The amount of tooth whitening composition will vary depending upon the intended use, the size of the substrate 22, concentration of the peroxide agent, and the desired benefit. Generally, less than about 1 gram is provided. In another embodiment, from about 0.05 grams to about 0.5 grams are provided and in yet another embodiment from about 0.1 gram to about 0.4 grams of the tooth whitening composition are provided. The amount of tooth whitening composition per square cm of substrate 22 is less than about 0.2 grams/cm$^2$, or from about 0.005 to about 0.1 grams/cm$^2$, or from about 0.01 grams/cm$^2$ to about 0.05 grams/cm$^2$.

As known in the art, the tooth whitening composition also has a yield stress. Yield stress is the amount of force on a material before the material begins to move. The yield stress must be high enough so that the tooth whitening composition is able to form a thin layer and also to handle the disturbances caused by manufacturing, handling, and storage. The yield stress of the tooth whitening composition is between about 2 Pascals and about 3000 Pascals, or between about 20 Pascals and about 2000 Pascals, or between about 200 Pascals and about 1500 Pascals, or between about 400 Pascals and about 1200 Pascals.

The tooth whitening agents suitable for use with the tooth whitening composition include peroxides, metal chlorites, perborates, peroxyacids, and combinations thereof. Peroxide agents can include hydrogen peroxide, calcium peroxide, carbamide peroxide, and mixtures thereof. Suitable metal chlorites include calcium chlorite, barium chlorite, magnesium chlorite, lithium chlorite, sodium chlorite, and potassium chlorite. Additional tooth whitening agents include hypochlorite and chlorine dioxide. While the tooth whitening agent can be present in any concentration, it is preferred that the peroxide agent is present in an concentration of hydrogen peroxide equivalent of at least about 0.01%, or at least about 0.1%, or at least about 0.5%, or at least about 5%, or at least about 8%, or at least about 10%, or at least about 12%, or at least about 15% and/or less than about 15%, or less than about 20%, or less than about 25%, or less than about 30% or less than about 40% by weight of the tooth whitening composition. It is understood that these concentrations are expressed for hydrogen peroxide and appropriate conversions must be made for other peroxide liberating molecules such as carbamide peroxide, calcium peroxide, etc.

Additional constituents of the tooth whitening composition can include, but are not limited to, water, gelling agents, humectants, pH adjusting agents, stabilizing agents, desensitizing agents, and accelerating agents or bleach activators. A common gelling agent is a swellable polymer. An effective concentration of a gelling agent to enable the tooth whitening composition to form a layer will vary with each type of gelling agent. The thin layer will have a viscosity and yield stress enabling the tooth whitening composition to form the thin layer on the substrate. The tooth whitening composition formed with these agents may also provide sufficient adhesive attachment of substrate to the targeted area of the mouth. For example, the level of gelling agent to form the tooth whitening composition with a carboxypolymethylene is between about 0.1% and about 15%, or between about 1% and about 10%, or between about 2% and about 8%, or between about 3% and about 6%, by weight of the tooth whitening composition. An effective concentration of a poloxamer gelling agent is between about 10% and about 40%, or between about 20% and about 35%, or between about 25% and about 30%, by weight of the tooth whitening composition.

Suitable gelling agents useful in the present invention include "Pemulen" made by Noveon, Inc., carboxypolymethylene, carboxymethyl cellulose, carboxypropyl cellulose, hydroxyethyl cellulose, poloxamer, Laponite, carrageenan, Veegum, carboxyvinyl polymers, and natural gums such as gum karaya, xanthan gum, Guar gum, gum arabic, gum tragacanth, and mixtures thereof. The preferable gelling agent for use in the present invention is carboxypolymethylene, obtained from B. F. Goodrich Company under the tradename "Carbopol". Particularly preferable Carbopols include Carbopol 934, 940, 941, 956, 971, 974, 980, and mixtures thereof. Particularly preferred is Carbopol 956. Carboxypolymethylene is a slightly acidic vinyl polymer with active carboxyl groups.

Other suitable gelling agents include both polymers with limited water solubility as well as polymers lacking water solubility. Suitable limited water solubility adhesives include: hydroxy ethyl or propyl cellulose. Adhesives lacking water solubility include: ethyl cellulose and polyox resins. Another possible adhesive suitable for use in the instant composition is polyvinylpyrrolidone with a molecular weight of about 50,000 to about 300,000. Still another possible adhesive suitable for use in the instant composition is a combination of Gantrez and the semisynthetic, water-soluble polymer carboxymethyl cellulose.

A pH adjusting agent may also be added to make the composition safe for oral tissues. These pH adjusting agents, or buffers, can be any material which is suitable to adjust the pH of the composition. Suitable materials include sodium bicarbonate, sodium phosphate, sodium hydroxide, ammonium hydroxide, potassium hydroxide, sodium stannate, triethanolamine, citric acid, hydrochloric acid, sodium citrate, and combinations thereof. The pH adjusting agents are added in sufficient concentrations so as to adjust the pH of the composition to between about 3 and about 10, or between about 4 and about 8.5, or between about 4.5 and about 8. The pH adjusting agents are generally present in an concentration between about 0.01% and about 15% or between about 0.05% and about 5%, by weight of the composition.

Suitable stabilizing agents include benzoic acid, salicylic acid, butylated hydroxytoluene, tin salts, phosphates, and others. Suitable bleach activators include trichloroisocyanuric acid and the phosphates, such as tetrasodium pyrophosphate.

Desensitizing agents may also be used in the tooth whitening composition. These agents may be preferred for consumers who have sensitive teeth. Desensitizing agents include potassium nitrate, citric acid, citric acid salts, strontium chloride, and combinations thereof. Potassium nitrate is a preferred desensitizing agent. Other agents which provide the benefit of reduced tooth sensitivity are also included in the present invention. Typically, the concentration of a desensitizing agent is between about 0.01% and about 10%, or between about 0.1% and about 8%, or between about 1% and about 7% by weight of the tooth whitening composition.

For a tooth whitening composition, it is often desirable to include a humectant as a constituent of the first composition. A humectant provides rheological and/or physical stability and provides various aesthetics for a user. Common humectants include polyols (e.g., glycerin, sorbitol, polyethylene glycol, propylene glycol). The polyol is present in a concentration of less than about 40%, or between about 0% and about 35%, or between about 1% and about 30%, or between about 5% and about 15%, by weight of the tooth whitening composition. As the concentration of polyol decreases, balance of the tooth whitening composition can comprise water. Generally, the concentration of water is at least about 0%, or at least about 25%, or at least about 50%, or at least about 60%, or at least about 70% and/or less than about 99%, or less than about 90%, or less than about 80%, or less than about 70% by weight of the total tooth whitening composition. This concentration of water includes the free water that is added plus that amount that is introduced with other materials.

The substrate 22 may be formed from materials such as polymers, natural and synthetic wovens, non-wovens, foil, paper, rubber, and combinations thereof. The substrate 22 may be a single layer of material or a laminate of more than one layer. In one embodiment, the substrate 22 is provided in the form of a substantially flat or planar strip of material. Suitable polymers include, but are not limited to, a polyolefins such as polyethylene or polypropylene, ethylvinylacetate, ethylvinyl alcohol, polyesters such as MYLAR® manufactured by DuPont, flouroplastics such as Teflon® manufactured by Dupont, and combinations thereof. Further, it is contemplated that the substrate 22 can be provided in the form of a roll rather than planar as shown FIG. 1. Alternatively, it is contemplated that the substrate 22 can be provided in other forms, such as preformed dental trays or flexible dental trays, wax, foams, hydratable films, porous webs or films, and combinations of any of the foregoing. Some of these other substrates are described in U.S. Pat. Nos. 6,419,906; 4,173,243; 5,310,563; 6,045,811; 5,326,685; 5,575,654; and RE 34,196, the substances of which are incorporated herein by reference.

While the substrate 22 can be sized according to its application and is generally sized for the oral cavity of a human user and more particularly, in the tooth whitening product 20, the substrate is sized to individually fit the tooth or row of teeth 40 desired to be bleached, as shown generally in FIGS. 6, 7, 8, and 9. Generally, this is the front, six to eight teeth of the upper or lower rows of teeth that are visible when the wearer is smiling or either the maxillary dentition or the mandibular dentition. Optionally, the substrate 22 may fit the entire upper or lower rows of teeth when positioned against the teeth. In one embodiment, the substrate 22 is sized to cover a portion of labial surface (i.e., front surface) and the soft tissue 42 adjacent the teeth and fold over the incisal edge of the teeth and onto at least a portion of the lingual surface (i.e., back surface) of the teeth. In another embodiment, the substrate 22 is further sized to cover at least the central six anterior teeth (canine/cuspid to canine/cuspid). The substrate 22 can be a maxillary strip which is rectangular with rounded corners and measures approximately 6.5 cm long×1.5 cm wide and/or the substrate 22 can be a mandibular strip which is trapezoidal with rounded corners and measures 5 cm long×2 cm wide. Further description of the size and shape of the substrate 22 in a tooth whitening application is disclosed in U.S. patent application Ser. No. 09/268,185 filed Mar. 15, 1999, now abandoned the substance of which is fully incorporated herein by reference.

In some embodiments, the substrate 22 should have a relatively low flexural stiffness so as to enable it to drape over the contoured surfaces of the teeth with very little force being exerted; that is, conformity to the curvature of the wearer's mouth, teeth, and gaps between teeth is maintained because there is little residual force within the substrate to cause it to return to its substantially flat shape. The flexibility of the substrate enables it to contact adjoining soft tissue over an extended period of time without physical irritation. The substrate does not require pressure to form it against the teeth and it is readily conformable to the tooth surfaces and the interstitial tooth spaces without permanent deformation when it is applied. When the substrate 22 is provided in the form of a thin, flexible strip, the substrate has a thickness of at least about 0.001 mm or at least about 0.005 mm and/or less than about 1 mm, or less than about 0.1 mm, or less than about 0.05 mm, or less than about 0.03 mm, or less than about 0.02 mm.

Flexural stiffness is a material property that is a function of a combination of substrate thickness, width, and material modulus of elasticity. This test is a method for measuring the rigidity of polyolefin film and sheeting. It determines the resistance to flexure of a sample by using a strain gauge affixed to the end of a horizontal beam. The opposite end of the beam presses across a strip of the sample to force a portion of the strip into a vertical groove in a horizontal platform upon which the sample rests. A microammeter, wired to the strain gauge is calibrated in grams of deflection force. The rigidity of the sample is read directly from the microammeter and expressed as grams per centimeter of sample strip width. In a preferred embodiment but not required for the present invention, the flexible substrate has a flexural stiffness of less than about 5 grams/cm as measured on a Handle-O-Meter, model #211-300, available from Thwing-Albert Instrument Co. of Philadelphia, Pa., as per test method ASTM D2923-95. Preferably, the substrate 22 has a flexural stiffness less than about 4 grams/cm, or less than about 3 grams/cm, or between about 0.1 grams/cm and about 1 grams/cm.

As discussed above, a release liner 32 can be optionally provided adjacent the first layer 28. The release liner 32 can be formed from any material which exhibits less affinity for the first layer 28 than the first layer 28 exhibits for itself and for the substrate 22. For example, the release liner 32 can be formed from paper or a polyester, such as SCOTCHPAK® which is manufactured by the 3M Corp. of Minneapolis, Minn., which are coated with a non-stick material in order to aid release of the tooth whitening composition from the release liner 32 when the substrate 22 is pulled away from the release liner 32. Exemplary coatings can include wax, silicone, fluoropolymers such as Teflon®, fluorosilicones, or other non-stick type materials. Also, suitable coatings might include one of the coatings described in U.S. Pat. Nos. 3,810,874; 4,472,480; 4,567,073; 4,614,667; 4,830,910; and 5,306,758, the substances of which are incorporated herein by reference. A further description of materials suitable which might be suitable as release agents is found in Kirk-Othmer Encyclopedia of Chemical Technology, Fourth Edition, Volume 21, pp. 207–218, incorporated herein by reference. While the release liner 32 should be at least the same size and shape as the substrate 22 as shown in FIG. 1, the release liner 32 can extend beyond the substrate so that it is easier to remove the substrate 22 (and the attendant first and second layers) from the release liner 32.

Figure 10:
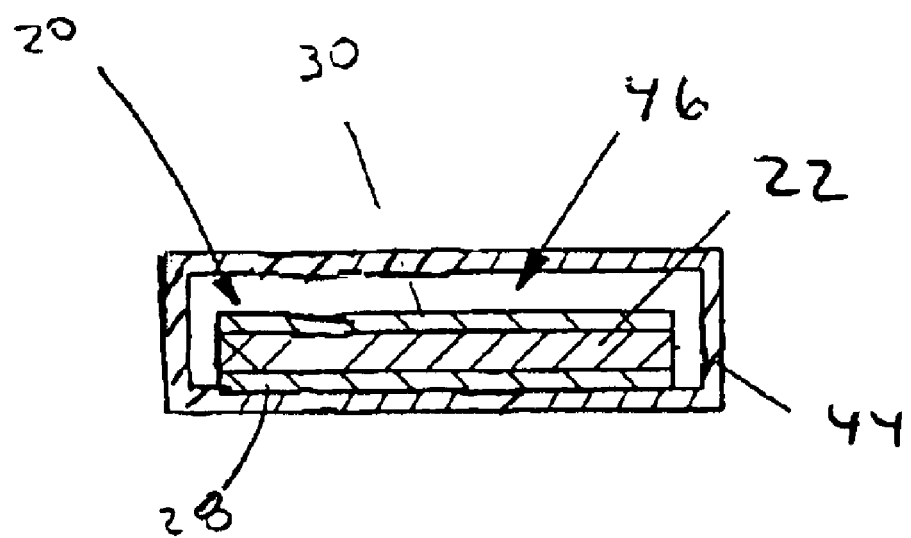
FIG. 10 is a cross-sectional side view of the tooth whitening product of FIG. 1 disposed within a package.

The tooth whitening product 20 may be disposed in a package 44, as shown in FIG. 10, which can be provided in a variety of shapes and sizes. However, it can be desirable that the shape and size of the package 44 closely conform to the shape and size of the tooth whitening product 20 and is sealed until ready for use. The package can be provided in the form of a pouch, a box, a plastic container, an envelope, a bag, or other suitable package known in the art. A plurality of packages 44 and tooth whitening products 20 can be bundled or otherwise provided as a set so that a sufficient supply of tooth whitening systems is available for multi-day use. More preferably, the volume of the headspace 46 of the package 44 is between about 0.1 mm$^3$ and about 30,000 mm$^3$ or between about 50 mm$^3$ and about 10,000 mm$^3$. The ratio of the volume of the headspace 46 to the volume of the first layer 28 is between 1 and about 500 and, preferably, is between 1 and about 400. More preferably, the ratio of the volume of the headspace 46 to the volume of the first layer 28 is between 1 and about 200 or between 1 and about 100. The package 44 should be made of a material that is not translucent, has low or no moisture permeability, and is generally impermeable. The package 44 may be made of one or more materials and may optionally have an interior liner. For example, a pouch could be made of foil and have a polyethylene inner lining. Other suitable materials that are not translucent and prevent moisture permeability include plastic, paper, foil, cardboard, polymers, and rubbers. A secondary package (not shown) can also be provided which stores a plurality of the packages 44.

In accordance with one aspect of the present invention, the second composition that forms the second layer 30 includes one or more aesthetic agents. The second composition can be provided in the form of a viscous liquid, a paste, a gel, a solution, a solid, a powder, or any other state or phase that can form a layer. As used herein, the phrase "aesthetic agent" refers to any agent that affects the gustatory, ofactory, or somatiosensory sensations. Examples of aesthetic agents include flavoring agents (e.g., sweetening agents, bitter agents, sour agents, etc.), aromatic agents (e.g., volatile oils and essences), and sensate agents (e.g., cooling agents, warming agents, etc.). These agents may be encapsulated, as discussed more fully hereafter, to reduce their diffusion from the second layer 30 into the headspace 46 of the package 44, to target delivery of the agents, to protect the agents from reactive substances such as water, peroxide, and other constituents of the tooth whitening product and package. Some suitable agents are described hereafter. While these agents have been described herein as flavoring agents, aromatic agents, and sensate agents for convenience, it will be appreciated that some agents may be classified in more than one category. For example, peppermint oil may be considered both an aromatic agent and a sensate agent (i.e., a cooling agent). Also, a plurality of aesthetic agents can be incorporated into the second layer 30. For example, it may be desirable to include a sweetener, such as sucralose, in combination with other aesthetic agents, such as menthol monophosphate (MMP) and N-ethyl-p-menthan-3-carboxamide (WS-3).

Suitable sweeteners include those well known in the art, including both natural and artificial sweeteners. Some suitable water-soluble sweeteners include monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin. Suitable water-soluble artificial sweeteners include soluble saccharin salts, i.e., sodium or calcium saccharin salts, cyclamate salts, the sodium, ammonium or calcium salt of 3,4-dihydro-6-methyl-1,2,3-oxathiazine-4-one-2, 2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include Dipeptide based sweeteners, such as L-aspartic acid derived sweeteners, such as L-aspartyl-L-phenylalanine methyl ester (aspartame) and materials described in U.S. Pat. No. 3,492,131, L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexyen)-alanine, and the like. Water-soluble sweeteners derived from naturally occurring water-soluble sweeteners, such as a chlorinated derivative of ordinary sugar (sucrose), known, for example, under the product description of sucralose as well as protein based sweeteners such as thaumatoccous danielli (Thaumatin I and II) can be used. In general, the composition forming the second layer 30 can contain greater than about 0%, or greater than about 0.001%, or greater than about 0.01%, or greater than about 0.5%, or greater than about 1%, or greater than about 10% or greater than about 25% or greater than about 50% and/or less than about 99%, or less than about 90%, or less than about 40%, or less than about 20%, or less than about 5%, or less than about 3% by weight of a sweetening agent. The upper sweetener range is generally applicable when the second layer 30 substantially comprises a sweetening agent in the form of a powder, as discussed more fully hereafter.

Cooling agents can be selected from any of a wide variety of materials. Included among such materials are carboxamides, menthol, ketals, diols, and mixtures thereof. Preferred cooling agents in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred cooling agents are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979; the disclosures of which are incorporated herein by reference. In general, the composition forming the second layer 30 contains greater than about 0%, or greater than about 0.001%, or greater than about 0.01%, or greater than about 0.1%, or greater than about 1%, or greater than about 10%, or greater than about 25%, or greater than about 50% and/or less than about 99%, or less than about 90%, or less than about 75%, or less than about 40%, or less than about 10%, or less than about 5%, or less than about 2% by weight of a cooling agent. The upper sweetener range is generally applicable when the second layer 30 substantially comprises a cooling agent in the form of a powder, as discussed more fully hereafter.

Natural and artificial aromatic agents can be used. Some suitable aromatic agents include synthetic oils, essential oils, oleo resins, essences, and extracts derived from plants, leaves, flowers, fruits and so forth, and combinations thereof. Representative oils include spearmint oil, cinnamon oil, oil of wintergreen, peppermint oil, clove oil, bay oil, eucalyptus oil, thyme oil, cedar leaf oil, oil of nutmeg, oil of sage, oil of bitter almonds. Also useful are artificial and natural fruit oils and essences, including vanilla, citrus, lemon, orange, grape, lime and grapefruit oils and fruit essences including apple, pear, peach, strawberry, raspberry, cherry, plum, pineapple, apricot, and so forth. These aromatic agents may be used individually or in admixture. Commonly used aromatic agents include mints (e.g., peppermint, menthol, spearmint, and wintergreen), cinnamon derivatives and various fruit oils or essences whether employed individually or in admixture. In general, the composition forming the second layer 30 contains greater than about 0%, or greater than about 0.001%, or greater than about 0.01%, or greater than about 0.1%, or greater than about 1% and/or less than about 60%, or less than about 30%, or less than about 15%, or less than about 5% by weight of an aromatic agent.

The aesthetic agents can also be combined, bound, or complexed with other elements and/or encapsulated. For example, a composition may be formulated by phosphorylating at least one aesthetic agent, such as an aromatic agent. These compositions are referred to herein as phosphate derivatives and are described more fully in WO 95/07683. Phosphate derivatives also include linking at least one aesthetic agent to an adherent component via a phosphate bridge. Pyrophosphate and triphosphate groupings may be substituted for the phosphate group. As used herein, the term "adherent component" is intended to refer to either monomers, oligomers, or polymers having hydroxy, amino, or thiol functionalities which are capable of forming either ester amido, or thioester linkages with phosphorus (V) atoms. The monomers, oligomers, or polymers may also possess additional hydroxy, amino, or thiol groups which may either remain unsubstituted or be linked via ester amido, or thioester linkages to a phosphorus (V) atom which is also attached to the aesthetic agent. Preferred compounds are selected from the group consisting of C12–C18 diacyl glycerol, partially hydrolized vinyl acetate/ethylene copolymer, cellulose, chitin, glucose, glucosamine, silica gel, gycerol, and lower alkyl vinyl ether-maleic acids. The aesthetic agent may also be linked to phosphorous via two functional groups or attachment sites or bound via Coulombic interaction with charged compounds or materials, including polymers.

The aesthetic agent of the phosphate derivative can be released after cleavage of the phosphate from the aesthetic agent by phosphatase enzymes, such as those commonly found in the oral cavity. The phosphatase enzymes include but are not limited to acid, basic, and pyrophosphatases. Preferred aesthetic agents including cooling agents selected from the group consisting of menthol, 3-1-menthoxypropane-1, 2-diol ("TK-10"), menthone glycercol acteal ("MGA"), and menthyl lactate. The terms "menthol" and "menthyl" as used herein include dextro- and levororatory isomers of these compounds and reacemic mixtures thereof. Preferred phosphate derivatives include menthyl monophosphate, menthol monophosphate, eugenyl monophosphate, thymyl monophosphate, 1-menthyl diphosphate, bis 1-menthyl pyrophosphate, and 1-mehtyl triphosphate. The phosphate derivatives can be represented by the following formula:

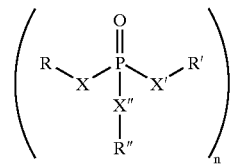

In the above formula,

R is selected is preferably selected from the group consisting of a cooling agent, a sweetening agent, and a flavoring agent;

R' and R" are independently selected from the group consisting of R, an adherent component, M+, M++, C+, and hydrogen;

M+ and M++ are metal cations that are significant to the organic or bodily processes of a human. Preferred M+ cations are sodium and potassium. Preferred M++ cations are zinc, magnesium, manganese, copper, and stannous.

C+ is an organic cation. An organic cation contains positively charged nitrogen, phosphorous, oxygen, or sulfur atoms. Such cations may contain more than one positively-charged site and in the case of oligomers or polymers containing nitorgen, phosphorous, oxygen, or sulfur atoms, many positively-charged centers may exist. Preferred organic cations include, ammonium, protonated amines such as protonated glucosamine, and partially or fully protonated amine-containing polymers such as protonate chitosan.

X, X', and X" are independently selected from the group consisting of oxygen, nitrogen, and sulfur; and n is an integer from 1 to 3.

In addition, R' may equal R", preferably wherein R' and R" are selected from the group consisting of calcium, zinc, and magnesium, manganese, copper, and stannous. Because the phosphate derivatives are highly stable and release the aesthetic agent only after cleavage of the phosphate from the aesthetic agent, phosphate derivatives are particularly preferred in the present invention.

The aesthetic agents may also be encapsulated in order to minimize diffusion from the second layer 30 into the headspace 46 of the package 44 or to increase the stability of the aesthetic agent. Suitable encapsulation agents include any of the known cyclodextrins, such as unsubstituted cyclodextrins containing from six to twelve glucose units, especially, alpha-, beta-, gamma-cyclodextrins, and mixtures thereof, and/or their derivatives, and/or mixtures thereof, that are capable of forming inclusion complexes with the above-described sensating agents. Alpha-, beta-, and gamma-cyclodextrins can be obtained from, among others, American Maize-Products Company (Amaizo), Hammond, Ind.; Roquette Corporation, Gurnee, Ill.; and Chinoin Pharmaceutical and Chemical Works, Ltd., Budapest, Hungary. There are many derivatives of cyclodextrins that are known. Representative derivatives include those disclosed in U.S. Pat. No. 3,426,011, Parmeter et al., issued Feb. 4, 1969; U.S. Pat. Nos. 3,453,257, 3,453,258, 3,453,259, and 3,453,260, all in the names of Parmerter et al., and all issued Jul. 1, 1969; U.S. Pat. No. 3,459,731, Gramera et al., issued Aug. 5, 1969; U.S. Pat. No. 3,553,191, Parmerter et al., issued Jan. 5, 1971; U.S. Pat. No. 3,565,887, Parmelter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,638,058, Brandt et al., issued Jan. 20, 1987; U.S. Pat. No. 4,746,734, Tsuchiyama et al., issued May 24, 1988; and U.S. Pat. No. 4,678,598, Ogino et al., issued Jul. 7, 1987, all of said patents being incorporated herein by reference. Examples of cyclodextrin derivatives suitable for use herein include methyl-β-CD, hydroxyethyl-β-CD, and hydroxypropyl-β-CD of different degrees of substitution (DS), available from, among others, Aldrich Chemical Company, Milwaukee, Wis.; Wacker Chemicals (USA), New Canaan, Conn.; and Chinoin Pharmaceutical Works, Budapest, Hungary. Water-soluble derivatives are also highly desirable.

The individual cyclodextrins can also be linked together, e.g., using multifunctional agents to form oligomers, polymers, etc. Examples of such materials are available commercially from Amaizo and from Aldrich Chemical Company (β-CD/epichlorohydrin copolymers). It may also be desirable to use mixtures of cyclodextrins to provide a mixture of complexes. Mixtures of cyclodextrins can conveniently be obtained by using intermediate products from known processes for the preparation of cyclodextrins including those processes described in U.S. Pat. No. 3,425,910, Armbruster et al., issued Feb. 4, 1969; U.S. Pat. No. 3,812,011, Okada et al., issued May 21, 1974; U.S. Pat. No. 4,317,881, Yagi et al., issued Mar. 2, 1982; U.S. Pat. No. 4,418,144, Okada et al., issued Nov. 29, 1983; and U.S. Pat. No. 4,738,923, Ammeraal, issued Apr. 19, 1988, all of said patents being incorporated herein by reference. Some cyclodextrin mixtures are commercially available from, e.g., Ensuiko Sugar Refining Company, Yokohama, Japan. The cyclodextrin complexes can be formed in any of the ways know in the art. Examples of such processes are described in U.S. Pat. Nos. 5,571,782; 3,812,011; 4,317,881; 4,418,144; and 4,378,923, the substances of which are incorporated herein by reference.

Other encapsulation technologies may also be used, such as microcapsules that comprise a core formed from an aesthetic agent and a coating layer over the core to control the release of the aesthetic agent. Coating materials that are water resistant and that release the aesthetic agent during use are preferred, including coating materials that fracture under physical forces such as chewing or that disperse or emulsify when contacted by saliva. Suitable coatings include those formed from gelatin, carboxymethyl cellulose, gum arabic, casein, alginate, waxes, lipids, and mixtures thereof. The coating layer can be prepared by coacervation which is a process for the aggregation of colloidal spheres held together by electrostatic forces and can be carried out by diluting an emulsion of the flavor oil in the presence of such colloidal materials with water, adjusting the pH of the emulsion or the temperature, or by any combination such techniques. U.S. Pat. Nos. 5,759,599; 5,266,335; 5,498,439; and 4,983,404; the substances of which are incorporated herein by reference, describe some encapsulation coatings and processes for forming the same that can be used with the present invention. Other processes known in the art can also be used (e.g., spray coating). Multiple encapsulations can be used with the present invention. For example, different encapsulation techniques could be used with different aesthetic agents that are both incorporated into the second layer 30 to provide differing release characteristics. Alternatively, several encapsulation techniques could be used to provide multiple layers of encapsulation about a single aesthetic agent.

The second composition can also comprise a carrier material for binding, attaching, or otherwise adhering the aesthetic agent to the substrate 22. In one embodiment, the carrier material facilitates formation of a film that is adherent to the substrate 22 but whose exposed side is non-adherent after formation on the substrate. Optionally, the exposed side of the second layer 30 can be coated with a lubricant to provide a non-adhesive surface. Suitable lubricant powders can include magnesium stearate, ethyl cellulose, and sodium stearyl fumarate. Further, the carrier material should facilitate the release of the aesthetic agent from the second layer 30 during use through dissolution, diffusion, dispersion, or other mechanism. Preferably, the carrier material is dispersible with saliva. The second layer has a thickness greater than about 0.005 mm, or greater than about 0.02 mm and/or less than about 1 cm, or less than about 5 mm, or less than about 2 mm, or less than about 1 mm, or less than about 0.1 mm. The overall thickness of the first layer, substrate, and second layer is greater than about 0.01 mm, or greater than about 0.05 mm, or greater than about 0.1 mm or greater than about 0.2 mm and/or less than about 3 mm, or less than about 2 mm, or less than about 1 mm, or less than about 0.5 mm, or less than about 0.4 mm, or less than about 0.3 mm, or less than about 0.2 mm. In general, the second composition contains at least about 0%, or at least about 10%, or at least about 25%, or at least about 50%, or at least about 75%, or at least about 95% and/or less than about 98%, or about 90%, or about 80%, or less than about 50%, or less than about 25%, or less than about 10% by weight of a carrier material. Suitable carrier materials can include in whole or part carbohydrates (e.g., hydroxy propyl methyl cellulose (HPMC), starch, arabic gum), lipids (e.g., fats and oils such as saturated and partially saturated vegetable oil, coconut oil, coca butter, Safflower oil, Palm Kernel oil, etc.), waxes (e.g., beeswax and Carnauba wax), hydrocarbons (e.g., petrolatum and mineral oils), silicones, proteins (e.g., casein and alginate), and combinations thereof. Carrier materials comprising carbohydrates, such as HPMC, are preferred when the aesthetic agent is non-volatile while carrier materials comprising a lipid or a hydrocarbon are preferred when the aesthetic agent is volatile.

The second layer 30 can be formed from combinations and/or derivatives of one or more carrier materials, or the layer 30 can be provided with multiple layers formed from distinct carrier materials and/or aesthetic agents. Further, it is contemplated that distinct second layers 30 can be formed at different locations on the substrate 22 or layered on top one another, wherein each second layer 30 is formed from distinct carrier materials and/or aesthetic agents. For example, a portion of the second layer might comprise hydroxy propyl methyl cellulose that dissolves quickly for a quick release of a first aesthetic agent and another portion of the second layer might comprise silicone that diffuses a second aesthetic agent over a longer period of time for sustained release of the second aesthetic agent. Or, the second layer 30 might comprise a first sub-layer comprising a first carrier material, such as a lipid, directly adjacent the substrate and a second sub-layer comprising a carbohydrate, such as HPMC, on top of the first sub-layer opposite the substrate, wherein the second sub-layer covers the first sub-layer. Since the second sub-layer comprising the HPMC is exposed to the oral cavity, it could provide improved feel for the user (e.g., a "non-sticky" outer layer) versus the first sub-layer comprising the lipid.

While the second layer 30 might incorporate a carrier material, it is contemplated that the second layer might merely be formed from a dry powder that adheres to the substrate 22 by electrostatic forces. The powder might be a dry, encapsulated aesthetic agent that is applied to the substrate by dusting, dry spraying, or other means known in the art. The powder might consist essentially of the aesthetic agent or the aesthetic agent in its encapsulated form, or the aesthetic agent might be admixed with other dry materials such as magnesium stearate, ethyl cellulose, and sodium stearyl fumarate.

Figure 11:
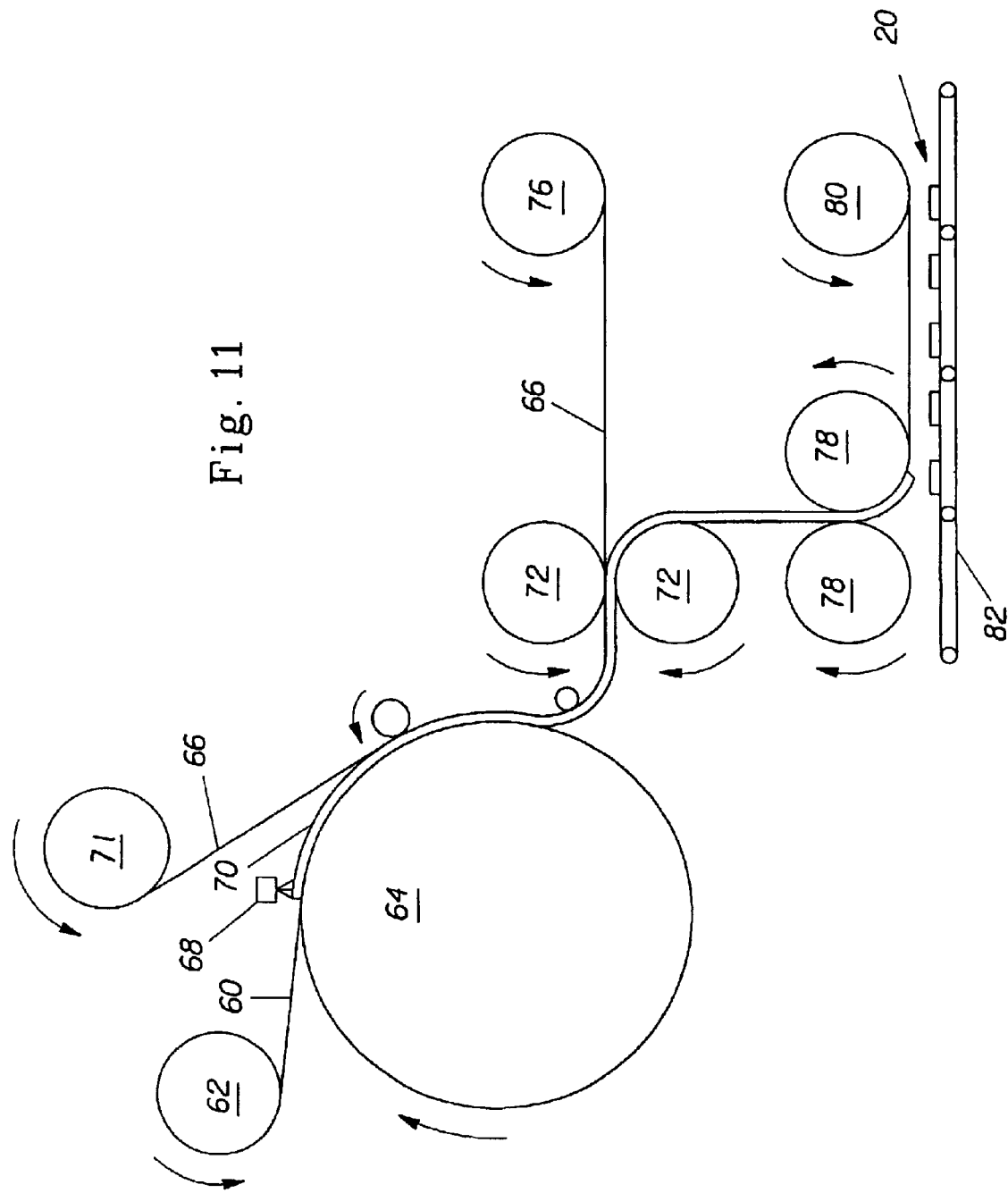
FIG. 11 is a schematic illustration of a process for manufacturing the embodiments of the present invention.

Referring to FIG. 11, a method for forming the tooth whitening product 20 will now be described. A sheet 60 of the release liner is unrolled from the roller 62 and is fed over drum 64. The sheet 60 of the release liner may be formed by several of the film making processes known in the art. The sheet 60 of the release liner (as well as sheet 66 of the substrate 22) may be formed by several of the film making processes known in the art. The sheets 60 and 66 can be made by a blown process or a cast process. Processes, such as extrusion and other processes that do not affect the flexural rigidity of the substrate might also be used. A nozzle 68 sprays the first layer 70 of the tooth whitening composition onto the sheet 60 of the release liner. The sheet 66 of the substrate 22 is unrolled from the roller 71 and lightly pressed onto the first layer 70 of the tooth whitening composition, thereby forming a three layer laminate. The laminate is fed to the rollers 72 which cut the outer edge of the substrate 22. After the cutting operation at rollers 72, the excess sheet 66 of the substrate 22 is taken up by the roller 76, thereby leaving the substrate 22 and the tooth whitening composition on the sheet 60 of the release liner. The rollers 78 cut the release liner to form individual tooth whitening products 20. The excess release liner is taken up by the roller 80 while the tooth whitening products 20 are collected by the conveyor 82, after which the tooth whitening products 20 can be inserted into a package to form a packaged tooth whitening product.

The second layer 30 can be formed before or after the formation of the first layer on the sheet 60. The second composition can be formed by admixing the aesthetic agent, the carrier material, a suitable solvent (e.g., food grade solvents like ethanol or ethyl acetate), and any other desired constituents (e.g., water and/or a humectant such as glycerol or propylene glycol). The mixture can be sprayed, via a nozzle, or otherwise coated onto the sheet 66 that is used to form the substrate. This can be done in separate process and the sheet 66 incorporating the second layer 30 can then be rolled and fed from roller 71. The second composition can be dried by, for example, a hot air convection process, to remove the solvent and adhere the second composition to the sheet 66 to form the second layer 30. If a solvent process is used to form the second layer, it is preferred that the second layer is formed on the sheet 66 before formation of the tooth whitening composition layer.

To practice the invention, a consumer opens the package and removes the tooth whitening product. The substrate is applied by the consumer to a plurality of adjacent teeth. The side of the substrate facing the teeth is coated with a tooth whitening composition that is preferably in a viscous state to provide not only the tooth whitening agent but also tackiness between the tooth surfaces and the substrate to hold the substrate in place for an extended period of time. The substrate is applied to the soft tissue adjacent the teeth and is folded over the incisal edges of the plurality of teeth and onto their lingual sides. The substrate readily conforms to the teeth by lightly pressing it against the teeth and/or by the consumer gently sucking through the gaps between the teeth. The substrate is easily removed by the wearer by peeling it off. Preferably, each successive treatment will use a fresh tooth whitening product. Since the second layer containing the aesthetic agent is directly exposed to the oral cavity (i.e., it is exposed to the lips and/or tongue during use), saliva can readily liberate the aesthetic agent thereby providing a pleasurable oral experience. The liberation of the aesthetic agent can be facilitated by movement of the tip of the tongue over the exposed surface of the second layer on one or both of the labial and lingual sides of the substrate when it is folded over the incisal edges of the teeth.

The tooth surface is not required to be prepared before the tooth whitening product is applied. For example, the wearer may or may not choose to brush his teeth or rinse his mouth before applying the delivery system. The surfaces of the teeth are not required to be dried or to be excessively wet with saliva or water before the substrate is applied. Preferably, the substrate and compositions are substantially transparent so as to be almost unnoticeable when worn. Thinness of the tooth whitening product enables the higher temperature inside of the wearer's mouth to conduct heat through the substrate to the normally cooler teeth in order to accelerate the rate of diffusion of the tooth whitening agent into the surfaces of the teeth. Preferably, the wearer applies the tooth whitening product to the teeth continuously for about 5 minutes to about 120 minutes a day, preferably from about 30 minutes to about 60 minutes. Generally, this is done once a day for about 7 to 28 consecutive days. The amount of time and the number of days are dependent upon several factors, including the amount of bleaching desired, the wearer's teeth, and if initial or maintenance bleaching is desired.

The following examples of a second composition further describe and demonstrate embodiments within the scope of the present invention. These examples are given solely for the purpose of illustration and are not to be construed as limitations of the present invention as many variations thereof are possible without departing from the spirit and scope of the present invention. Percentages herein are by weight unless otherwise stated.

EXAMPLE 1

A second composition is prepared having the following components:

| Component | Wet Basis (wt./wt. %) | Dry Basis (wt./wt. %) |
|---|---|---|
| Glycerine | 1.5 | 23.01 |
| Propylene Glycol | 0.4 | 6.13 |
| Sucralose | 0.65 | 9.97 |
| Menthol Monophosphate (MMP) | 1.45 | 22.24 |
| N-ethyl-p-methan-3-carboxamide (WS-3) | 0.32 | 4.91 |
| Purified water | 25.78 | 0 (evaporated) |
| Ethanaol, USP 200 Pf. | 67.7 | 0 (evaporated) |
| Hydroxy Propyl Methyl Cellulose (Methocel ®) | 2.2 | 33.74 |
| Total | 100 | 100 |

EXAMPLE 2

A second composition is prepared having the following components:

| Component | Wet Basis (wt./wt. %) | Dry Basis (wt./wt. %) |
|---|---|---|
| Glycerine | 1.5 | 3.3 |
| Propylene Glycol | 0.4 | 0.9 |
| Sucralose | 0.65 | 1.4 |
| Menthol Monophosphate (MMP) | 40 | 88.7 |
| N-ethyl-p-methan-3-carboxamide (WS-3) | 0.32 | 0.8 |
| Purified water | 25.78 | 0 (evaporated) |
| Ethanaol, USP 200 Pf. | 29.15 | 0 (evaporated) |
| Hydroxy Propyl Methyl Cellulose (Methocel ®) | 2.2 | 4.9 |
| Total | 100 | 100 |

EXAMPLE 3

A second composition is prepared having the following components:

| Component | Wet Basis (wt./wt. %) | Dry Basis (wt./wt. %) |
|---|---|---|
| White Petrolatum USP (Ultima ®) | 89.4 | NA |
| Sucralose | 0.6 | NA |
| Wintergreen oil | 10 | NA |
| Total | 100 | |

EXAMPLE 4

A second composition is prepared having the following components:

| Component | Wet Basis (wt./wt. %) | Dry Basis (wt./wt. %) |
|---|---|---|
| White Petrolatum USP (Ultima ®) | 73 | NA |
| Sucralose | 2 | NA |
| Spearmint oil | 25 | NA |
| Total | 100 | |

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A packaged tooth whitening product, comprising:
   a package;
   a substrate having a first side and a second side opposite said first side, wherein said substrate is disposed within said package and wherein said substrate is sized for use in a human user's oral cavity;
   a first composition comprising a peroxide agent, wherein said first composition is disposed adjacent said first side of said substrate; and
   a second composition comprising an aesthetic agent, wherein said second composition is disposed as a layer or plurality of layers adjacent said second side of said substrate and wherein said layer or plurality of layers releases said aesthetic agent during said use.

2. The packaged tooth whitening product of claim 1, wherein said aesthetic agent is selected from the group consisting of flavoring agents, aromatic agents, sensate agents, and combinations thereof.

3. The packaged tooth whitening product of claim 1, wherein aesthetic agent is encapsulated.

4. The packaged tooth whitening product of claim 1, wherein said aesthetic agent is phosphorylated aesthetic agent.

5. The packaged tooth whitening product of claim 4, wherein said phosphorylated aesthetic agent is menthol monophosphate.

6. The packaged tooth whitening product of claim 1, wherein said second composition comprises a carrier material selected from the group consisting of carbohydrates, lipids, waxes, hydrocarbons, silicones, proteins, combinations thereof, and derivatives thereof.

7. The packaged tooth whitening product of claim 1, wherein said layer or plurality of layers has a thickness between about 0.005 mm and about 2 mm.

8. The packaged tooth whitening product of claim 1, wherein said tooth whitening agent is a peroxide agent and wherein said first composition further comprises water.

9. The packaged tooth whitening product of claim 1, wherein said aesthtic agent is a sweetener and the concentration of said sweetener is between about 0.01% and about 40% by weight of said second composition.

10. The packaged tooth whitening product of claim 1, further comprising a second aesthetic agent.

11. The packaged tooth whitening product of claim 10, wherein said second aesthetic agent is a cooling agent and the concentration of said cooling agent is between about 0.001% and about 40% by weight of said second composition.

12. The packaged tooth whitening product of claim 1, wherein said substrate is a planar strip of material.

13. The packaged tooth whitening product of claim 1, wherein said second composition is provided in the form of a powder.

14. The packaged tooth whitening product of claim 13, wherein said second composition consists essentially of said aesthetic agent.

15. The packaged tooth whitening product of claim 13, wherein the concentration of said aesthetic agent is between about 50% and about 90% by weight of said second composition.

16. The packaged tooth whitening product of claim 1, wherein said substrate comprises a wax.

17. The packaged tooth whitening product of claim 1, wherein said substrate is provided in the form of a film.

18. The packaged tooth whitening product of claim 1, wherein said substrate comprises a polyolefin.

19. The packaged tooth whitening product of claim 1, wherein said layer or plurality of layers is formed into distinct sections at different locations on said substrate.

20. The packaged tooth whitening product of claim 1, wherein said second composition comprises a plurality of layers.

* * * * *